US00PP21683P2

(12) United States Plant Patent
Pedersen

(10) Patent No.: US PP21,683 P2
(45) Date of Patent: Jan. 25, 2011

(54) *LAVANDULA* PLANT NAMED 'GREEN SUMMER'

(50) Latin Name: *Lavandula stoechas*
Varietal Denomination: Green Summer

(75) Inventor: Jens Ingemann Pedersen, Odense N. (DK)

(73) Assignee: Tvillingegarden A/S, Odense N. (DK)

( * ) Notice: Subject to any disclaimer, the term of this patent is extended or adjusted under 35 U.S.C. 154(b) by 0 days.

(21) Appl. No.: 12/462,814

(22) Filed: Aug. 10, 2009

(51) Int. Cl.
*A01H 5/00* (2006.01)

(52) U.S. Cl. ..... Plt./445

(58) Field of Classification Search ..... Plt./263, Plt./445

See application file for complete search history.

*Primary Examiner*—Susan B McCormick Ewoldt
(74) *Attorney, Agent, or Firm*—Jondle & Associates, P.C.

(57) ABSTRACT

A *Lavandula* cultivar particularly distinguished by a compact and rounded plant habit, a globular plant shape with low to moderate vigor, violet-blue flowers with a continuous and rich flowering habit, and a flowering habit that when the first flowers are trimmed, the plant will flower again, is disclosed.

3 Drawing Sheets

Genus and species: *Lavandula stoechas.*
Variety denomination: 'Green Summer'.

BACKGROUND OF THE NEW PLANT

The present invention comprises a new and distinct cultivar of *Lavandula*, botanically known as *Lavandula stoechas*, and hereinafter referred to by the cultivar name 'Green Summer'. The new cultivar originated from an open pollination of the female *Lavandula stoechas* parent 'Avenue' (unpatented) among un-named *Lavandula stoechas* plants (unpatented) in Odense, Denmark in summer 2006.

The new cultivar was created in summer 2006 in Odense, Denmark, and has been asexually reproduced repeatedly by softwood cuttings in Odense, Denmark for at least two generations The present invention has been found to retain its distinctive characteristics through successive asexual propagations.

'Green Summer' has not been made publicly available or sold more than one year prior to filing of this application.

SUMMARY OF THE INVENTION

The following are the most outstanding and distinguishing characteristics of the new cultivar when grown under normal horticultural practices in Mijdrecht, The Netherlands.

1. A compact and rounded plant habit;
2. A globular plant shape with low to moderate vigor;
3. Violet-blue flowers with a continuous and rich flowering habit; and
4. A flowering habit that when the first flowers are trimmed, the plant will flower again.

DESCRIPTION OF THE PHOTOGRAPHS

This new *Lavandula* plant is illustrated by the accompanying photographs which show overall plant habit including inflorescences, buds, and foliage of the plant. The colors shown are as true as can be reasonably obtained by conventional photographic procedures. The photos are of a 2-year-old plant grown in a 2.0 liter container in Odense, Denmark in May 2009.

DESCRIPTION OF THE NEW CULTIVAR

Figure 1:
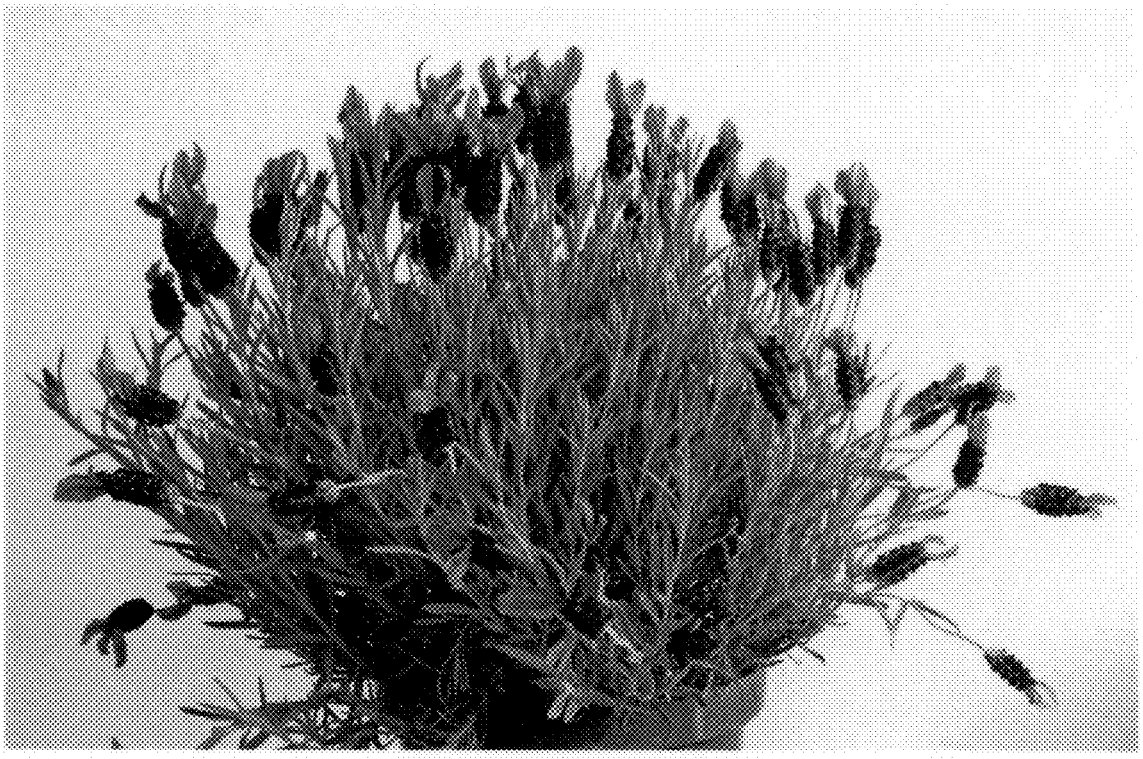
FIG. 1 shows the overall plant habit including inflorescences and foliage.
Figure 2:
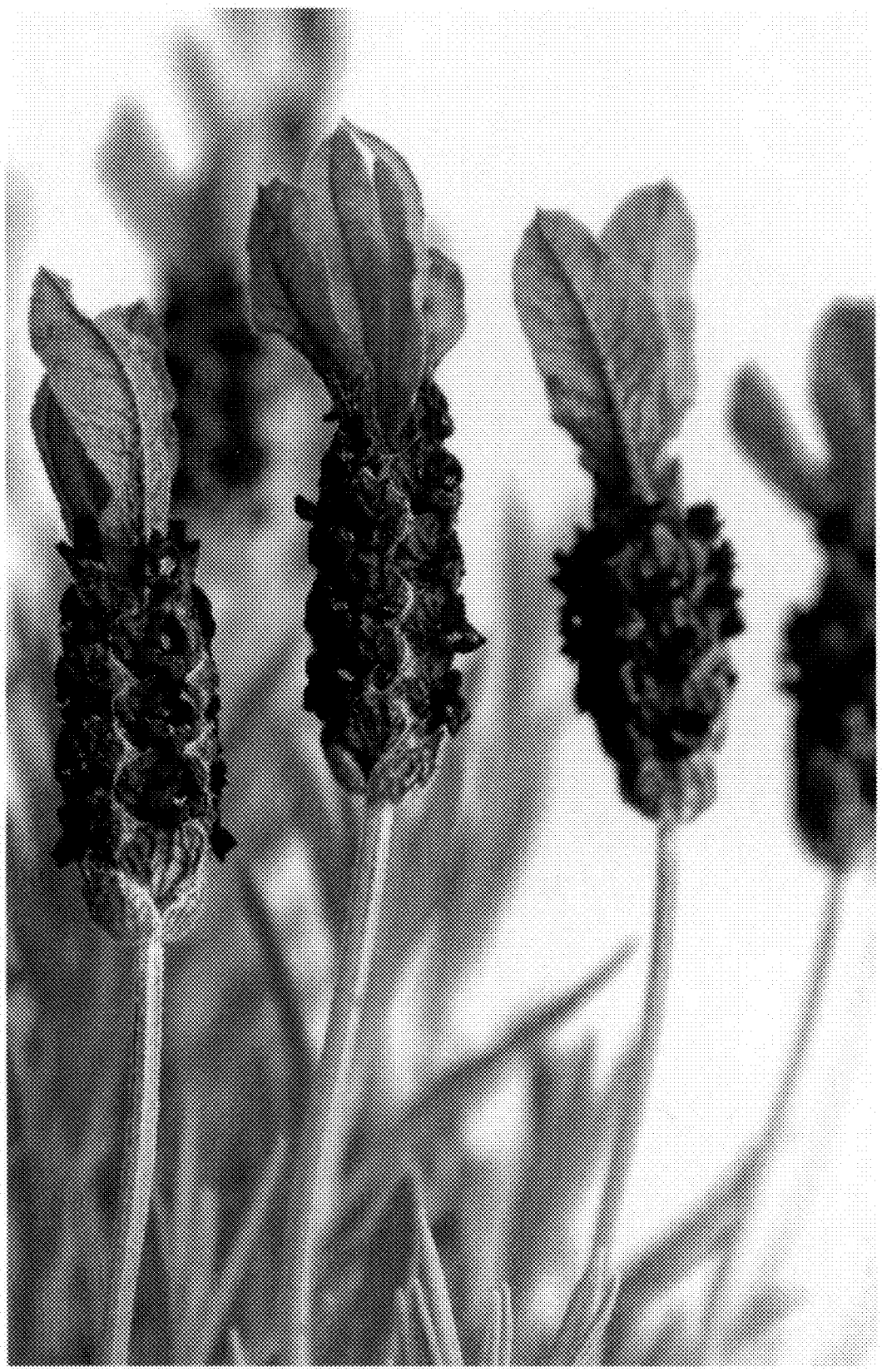
FIG. 2 shows a close-up view of the inflorescences.
Figure 3:
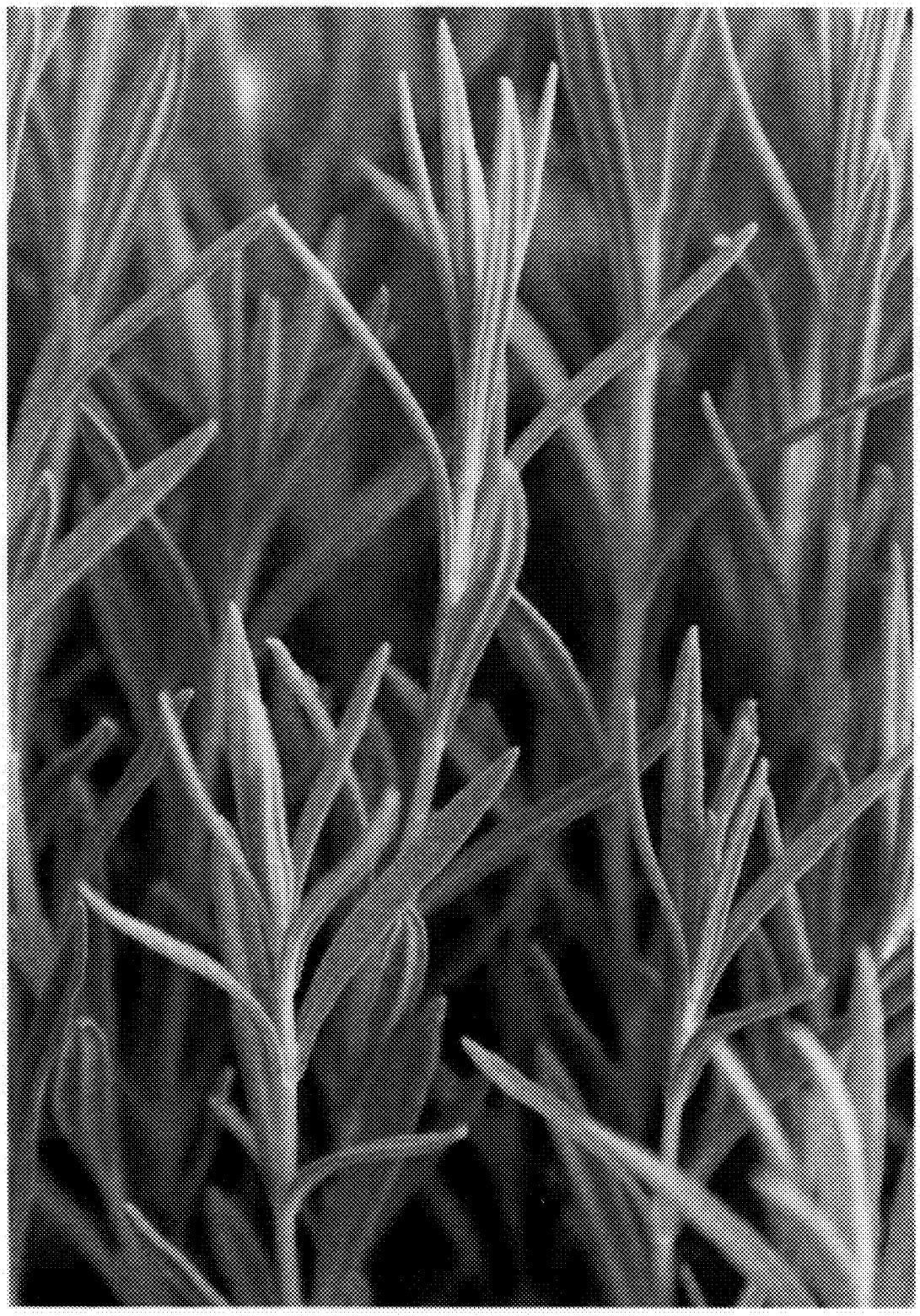
FIG. 3 shows a close-up view of the mature leaves.

The following detailed descriptions set forth the distinctive characteristics of 'Green Summer'. The data which define these characteristics were collected from asexual reproductions carried out in Mijdrecht, The Netherlands. The plant history was taken on 2-year-old plants grown in 2.0 liter containers outdoors in April 2009. The range of daytime temperature was 12° C. to 27° C. and the range of night-time temperature was from 5° C. to 15° C. No growth retardants were used. The color readings were determined under natural light. Color references are to The R.H.S. Colour Chart of The Royal Horticultural Society of London (R.H.S.) (2007).

DESCRIPTION OF THE NEW PLANT

Classification:

*Family.*—Lamiaceae.

*Botanical name.*—*Lavandula stoechas.*

*Common name.*—French lavender, topped lavender.

*Denomination.*—'Green Summer'.

Plant:

*Form and habit.*—Perennial subshrub.

*Growth and branching habit.*—Broadly upright and free-branching.

*Plant shape.*—Globular.

*Height* (*from top of soil, including inflorescences*).—28.9 cm.

*Width* (*spread*).—41.4 cm.

*Vigor.*—Low to moderate.

*Growth rate.*—Approximately 4.0 cm per month in the spring.

*Time to produce a rooted cutting or liner in summer.*—About 85 days at 16° C. to 18° C.

*Time to produce a finished flowering plant.*—About 32 weeks from a rooted cutting.

*Outdoor plant performance.*—Use in 12.0 cm pots or larger or in flower beds.

*Fragrance.*—All parts of the plant are strongly aromatic with a fragrance typical of *Lavandula stoechas.*

*High temperature tolerance.*—At least up to 40° C.

*Low temperature tolerance.*—Hardy to at least USDA Zone 7.

*Roots.*—Moderately dense and dark brown; young roots are white and fading to yellow-brown; main roots are thick while other roots are fine; about 15 to 18 days to initiate roots in the summer at 17° C.

Stems:

*Branching.*—Basal; free-branching.

*Total number of lateral branches.*—146.

*Length* (*excluding inflorescence*).—10.5 cm.

*Diameter.*—0.2 cm.

*Internode length.*—1.2 cm.

*Appearance/shape.*—Quadrangular and dull.

*Strength.*—Strong.

*Color.*—RHS 144B and RHS 144C (Yellow-green); older bark is RHS N199B (Greyed-brown).

*Texture.*—Tomentose; moderately dense covered with wooly hairs. Length of hairs: 0.02 cm. Color of hairs: RHS 145D (Yellow-green).

Leaves:

*Arrangement.*—Single and opposite.

*Quantity per lateral branch.*—16 (8 pairs).

*Shape.*—Linear, carinate.

*Apex.*—Acute.

*Base.*—Cuneate.

*Margin.*—Entire.

*Texture and appearance* (*both surfaces*).—Moderately wooly tomentose and dull; length of pubescence is 0.02 cm and pubescence color is RHS 191D (Greyed-green).

*Size.*—Length: 3.2 cm. Width: 0.4 cm.

*Immature leaf.*—Color: Upper surface: RHS 137D (Green). Lower surface: RHS 138B and RHS 138C (Green).

*Mature leaf.*—Color: Upper surface: RHS 137B (Green). Lower surface: RHS 191A (Greyed-green).

*Venation.*—Pinnate.

*Vein color.*—Upper surface: RHS 194B (Greyed-green). Lower surface: RHS 191B (Greyed-green).

*Petioles.*—Absent, leaves are sessile.

*Durability of foliage to stresses.*—High.

Inflorescence buds:

*Shape.*—Narrow-oblong.

*Length.*—0.7 cm.

*Diameter.*—0.2 cm.

*Rate of opening.*—Approximately 3 days.

*Color.*—RHS 148A (Yellow-green); the base is lighter, RHS 144C and RHS 144D (Yellow-green); the tip is RHS 184B and RHS 184C (Greyed-purple).

*Quantity per lateral stem.*—108.

Inflorescence:

*Type and form.*—Spike and single.

*Arrangement.*—Terminal spike.

*Inflorescence size.*—Height: 5.3 cm (excluding peduncle). Width: 1.5 cm but the sterile bracts on top of the spikes have an average spread of 2.4 cm.

*Quantity of flowers per inflorescence.*—108.

*Quantity of open inflorescences and buds per plant.*—15,000.

*Blooming habit.*—Blooms once per year, continuously, during the spring to later summer.

*Rate of inflorescence opening.*—Approximately 30% of the flowers are open at any given time.

Flower:

*Aspect.*—Outward.

*Type and appearance.*—Self-cleaning; individual flowers are sessile (no pedicels).

*Shape.*—Salverform, with one upper petal (split into two identical lobes) and one lower petal (split into three lobes, identical to upper lip).

*Size.*—Depth (height): 1.1 cm. Diameter: 0.4 cm.

*Flower longevity on the plant.*—About 10 days.

*Quantity of flowers per lateral stem.*—108.

Petals:

*Arrangement.*—Rotate.

*Quantity.*—2.

*Shape.*—Spathulate with the lower 70% of each petal fused into a tube.

*Apex.*—Rounded.

*Base.*—Fused.

*Margin.*—Entire.

*Texture* (*both surfaces*).—Dull and smooth.

*Size.*—Length: 1.1 cm. Width: Upper lip petals are 0.3 cm and lower lip petals are 0.4 cm.

*Color when opening and fully opened* (*both surfaces*) .—Between RHS N92A (Violet-blue) and RHS N92C (Violet-blue) but slightly darker; the tube is RHS N155A (White).

*Color, fading to.*—RHS N92A (Violet-blue) but slightly darker.

*Peduncle.*—Length: 7.1 cm. Diameter: 0.2 cm. Angle: 0 degrees; peduncle is straight and upright. Strength: Strong. Color: RHS 144B and RHS 144C (Yellow-green) but moderately covered with a woolly pubescence which is RHS 145D (Yellow-green).

Calyx:

*Shape.*—Campanulate tube.

*Length.*—0.6 cm.

*Diameter:* 0.15 cm.

*Sepals.*—Quantity: 5. Arrangement and shape: Linear and fused into a campanulate tube. Appearance and texture: Dull, densely woolly tomentose; pubescence is less than 0.02 cm long and is RHS 192D (Greyed-green). Apex: Acute. Base: Fused. Margin: Entire. Size: Length: 0.6 cm. Width: 0.1 cm. Color, immature: Upper surface: RHS 148C (Yellow-green) and the base is lighter, RHS 144D (Yellow-green). Lower surface: RHS 148A (Yellow-green) and the base is lighter, between RHS 144C and RHS 144D (Yellow-green). Color, mature: Upper surface: RHS 148C (Yellow-green) with RHS 148A stripes; the base is lighter, RHS 145C and RHS 145D (Yellow-green). Lower surface: RHS 148A (Yellow-green) and the base is lighter, RHS 145C and RHS 145D (Yellow-green); one side is shaded RHS 182B (Greyed-red).

Bracts:

*Fertile.*—Location: At the base of each individual flower. Shape: Broad rhomboidal. Quantity per inflorescence: 1. Margin: Entire. Apex: Broadly acute and 3-lobed. Base: Cuneate. Texture (both surfaces): Dull, moderately woolly, tomentose; pubescence is about 0.02 cm long and RHS 157D (Green-white). Length: 0.9 cm. Width: 0.8 cm. Color, upper surface: RHS 148D (Yellow-green) with darker RHS 148A veins. Color, lower surface: RHS 71A (Red-purple) with RHS N186A (Greyed-purple) veins.

*Sterile.*—Location: On top of each spike. Quantity per inflorescence: 4. Shape: Narrow obovate. Margin: Wavy. Apex: Broadly acute. Base: Cuneate. Texture (both surfaces): Dull and smooth. Length: 2.8 cm. Width: 0.9 cm. Color (both surfaces): RHS 83C (Violet) but with a slightly lighter RHS N92A (Violet-blue) main vein.

Reproductive organs:

*Stamens.*—Number: 4. Filament length: 0.05 cm. Filament color: RHS N92C (Violet-blue). Anther shape: Dorsifixed, kidney-shaped; filament implanted in the petal. Anther length: 0.05 cm. Anther color: RHS 165B (Greyed-orange). Pollen color: Close to RHS 164A and RHS 164B (Greyed-orange). Pollen amount: Sparse.

*Pistil.*—Quantity: 1. Pistil length: 0.4 cm. Stigma color: RHS N186A (Greyed-purple). Stigma shape: Club-shaped. Style color: RHS 155C (White). Style length: 0.35 cm. Ovary color: RHS 145D (Yellow-green).

Fruit and seed set: No seed set observed.

Disease and insect resistance: Average/typical of the species; no special observations made.

COMPARISON WITH PARENTAL AND COMMERCIAL CULTIVARS

'Green Summer' differs from the female parent 'Avenue' (unpatented) in that 'Green Summer' has a more rounded plant habit and is shorter in height than 'Avenue'. Additionally, 'Green Summer' has shorter peduncles and shorter bracts than 'Avenue'.

'Green Summer' differs from the commercial comparison variety 'Dream' (U.S. Plant Pat. No. 18,941) in that 'Green Summer' has a wider plant diameter (41.4 cm) than 'Dream' (30.48 cm). Additionally, 'Green Summer' has larger leaves (3.2 cm long and 0.4 cm wide) than 'Dream' (2.7 cm to 3.0 cm long and 0.3 cm wide).

I claim:

1. A new and distinct cultivar of *Lavandula* plant as shown and described herein.

* * * * *